United States Patent [19]

Zacharski et al.

[11] Patent Number: 4,665,499

[45] Date of Patent: May 12, 1987

[54] AVERAGING METHOD FOR PERIODIC STRAYS ELIMINATION AND A COUNTING CIRCUIT FOR EVOKED RESPONSES MEASURING SET-UP FOR APPLYING THE METHOD

[75] Inventors: Bogdan W. Zacharski; Piotr H. Siarkiewicz, both of Warsaw, Poland

[73] Assignee: Instytut Psychoneurologiczny, Warsaw, Poland

[21] Appl. No.: 577,677

[22] Filed: Feb. 7, 1984

[51] Int. Cl.⁴ .......................... G06G 7/12; A61B 5/04; G06F 15/42
[52] U.S. Cl. .................................. 364/575; 364/574; 364/417; 128/731
[58] Field of Search ................ 364/575, 574, 413–417; 128/702, 703, 710, 731, 734

[56] References Cited

U.S. PATENT DOCUMENTS

| | | | |
|---|---|---|---|
| 3,087,487 | 4/1963 | Clynes | 128/731 |
| 3,901,215 | 8/1985 | John | 128/731 |
| 4,171,696 | 10/1979 | John | 128/731 |
| 4,199,817 | 4/1980 | Conkling et al. | 364/575 |
| 4,326,539 | 4/1982 | Obermajer | 364/415 |
| 4,407,959 | 10/1983 | Tsuji et al. | 364/415 |
| 4,462,411 | 7/1984 | Rickards | 128/731 |
| 4,543,957 | 10/1985 | Friedman et al. | 364/413 X |
| 4,561,449 | 12/1985 | Hu et al. | 128/746 |

OTHER PUBLICATIONS

Bendat, J. S., "Mathematical Analysis of Average Responses Values for Nonstationary Data", IEEE Transactions of Bio-Medical Engineering, BME-11; 72–81, 1964.

Kopéc, J., Polish Computer 'ANOPS' for Medical Research and its Clinical Application", Acta Physiologica Polonica, 21:113–123, 1970.

Sim et al, "A Microcomputer Based Signal Averaging System with Applications in Medicine", Australasian Physical Science in Medicine, vol. 2-6, No. 83, Aug. 1979, pp. 338–345.

Primary Examiner—Felix D. Gruber
Assistant Examiner—Joseph L. Dixon
Attorney, Agent, or Firm—Ladas & Parry

[57] ABSTRACT

An averaging method for elimination of periodic stray signals, such as stray signals originating ain an environment (2) comprising a main signal source, which method is employed in a system for measuring evoked responses during an averaging procedure run in an averaging computer (7) which processes a set of signals picked up from an examined subject (10), e.g. a human scalp, by means of electrodes (11) which set of signals is fed through an instrumentat ion amplifier (9) to an averaging computer (7). A counting circuit in the system for measuring evoked responses comprises a sensing circuit (1), a circuit (3) detecting signal half-periods, a counting circuit (5) and a triggering circuit (6), and introduces permanent desynchronization between the frequency 1/T of external stimuli signals, e.g. from a photostimulator (8), and the sweeps of the averaging procedure in the averaging computer (7) both in relation to the frequency 1/T of the periodic stray signals resulting in amplitudes of the stray signals being substantially completely eliminated.

3 Claims, 5 Drawing Figures

AVERAGING METHOD FOR PERIODIC STRAYS ELIMINATION AND A COUNTING CIRCUIT FOR EVOKED RESPONSES MEASURING SET-UP FOR APPLYING THE METHOD

CROSS REFERENCE TO RELATED APPLICATION

This application is related to the applicants' copending application, Ser. No. 577,671 filed Feb. 7, 1984 entitled "Averaging Method for Elimination of Periodic Strays and a Circuit Arrangement for Applying the Method.

BACKGROUND OF THE INVENTION

The present invention relates to an averaging method for elimination of periodic strays, e.g. stray signals from a main signal source and a circuit arrangement in a system measuring evoked responses for applying the method.

The averaging method for elimination of periodic strays, e.g. stray signals from a main signal source is suitable for use in analog-digital computers employing an averaging procedure. The averaging procedure elicits evoked responses from a set of signals $U_{zs}$ recorded from an examined subject. The set of signals $U_{zs}$ comprises: internal noise $U_{szw}$; individual evoked responses $U_{ow}$ from the examined subject; and periodic strays $U_{zp}$ induce in this subject from an environment comprising a source of the mentioned strays, the specified components of the set of signals being independent.

The above statements on the set of signals $U_{zs}$ can be presented by the following formula: $U_{zs}=U_{szw}+U_{ow}+U_{zp}$. The set of signals $U_{zs}$ does not comprise the component of apparatus noise $U_{sza}$ resulting from the operation of the apparatus which picks up and amplifies the set of signals $U_{zs}$, because the apparatus internal noise should be so small as to be neglected within the set of signals $U_{zs}$ during its continuous monitoring e.g. when observing this set on a monitor screen of an averaging computer. This noise can be recognised as the characteristic white noise, which due to its properties is non-synchronous with the aforementioned signals $U_{zs}$.

The mathematical basis of the averaging procedure has been described in a publication by J. S. Bendat: "Mathematical Analysis of Average Response Values for Non-stationary Data", IEEE Transactions on Bio-Medical Engineering, BME-11: 72–81, 1964, and its technicalclinical realization has been described by J. Kope : "Polish Computer ANOPS for Medical Research and its Clinical Application", Acta Physiologica Polonica, 21: 113–123, 1970.

Hitherto both the internal noise $U_{szw}$ of the examined subject and the periodic strays $U_{zp}$ were considered to be non-synchronous signals in relation to the individual evoked responses $U_{ow}$ and the averaging procedure could be described by the following formula:

$$\overline{U_{zs}} = \frac{1}{N}\left[\sum_{n=1}^{N} U_{ow} + \frac{1}{\sqrt{N}} \sum_{n=1}^{N}(U_{szw}+U_{zp})\right]$$

$$= \overline{U_{ow}} + \frac{1}{\sqrt{N}}\overline{(U_{szw}+U_{zp})}$$

$$\approx \overline{U_{ow}}$$

where n = 1, 2, 3, . . . , N; N at least several hundred.

As an example of the above-mentioned situation, with 256 sweeps of the averaging procedure, the square root of N equals sixteen, and with maximum amplitudes of the internal noise $U_{szw}$ and of the periodic strays $U_{zp}$ equal to 64 μV then their reduction as a result of the averaging procedure is sixteen-fold, thus their maximum averaged amplitudes $\overline{U_{szw}}$ and $\overline{U_{zp}}$ are not greater than 4 μV.

According to the above, the averaging procedure, from the practical viewpoint, efficiently reduces the noise and the strays when the ratio of the maximum amplitudes of the noise and strays to the least significant amplitudes of the individual evoked responses is less than 20:1 and the reduction is proportional to the square root of the number of sweeps of the averaging procedure provided that the noise and strays are non-synchronus in relation to the individual evoked responses.

In unfavourable measuring conditions, even if the requirements regarding the said ratio are fulfilled, amplitudes of the periodic strays $U_{zp}$ may become comparable with amplitudes of the individual evoked responses $U_{ow}$ and the strays may become synchronous in relation to the individual evoked responses $U_{ow}$, so that the averaged but nevertheless significant periodic strays $\overline{U_{zp}}$ can be superimposed on the averaged evoked response $\overline{U_{ow}}$. The superimposed signal may distort the averaged response to such an extent that its waveform is difficult to interpret.

The above-described situation can be described by the following formula:

$$\overline{U_{zs}} = \frac{1}{N}\left[\sum_{n=1}^{N}(U_{ow}+U_{zp}) + \frac{1}{\sqrt{N}}\sum_{n=1}^{N} U_{szw}\right]$$

$$= \overline{(U_{ow}+U_{zp})} + \frac{1}{\sqrt{N}}\overline{U_{szw}} \approx \overline{U_{ow}+U_{zp}}$$

where n = 1, 2, 3, . . . , N; N at least several hundred.

As an example of the above-described situation, with 256 sweeps of the averaging procedure the square root of N equals sixteen and where the maximum amplitudes of the internal noise $U_{szw}$ and of periodic strays $U_{zp}$ are equal to 64 μV then the sixteen-fold reduction in the averaging procedure is effective only in respect of the averaged internal noise $U_{szw}$ resulting in its amplitude not exceeding 4 μV, while the averaged periodic strays $\overline{U_{zp}}$ behave as the averaged evoked response $\overline{U_{ow}}$, are not reduced, and remain equal to 64 μV. In such a case, other known means for reduction of noise and various strays are commonly used, i.e, analog and/or digital filtering means. The known filter circuits may be divided into: low-pass filters—eliminating strays and higher frequency signals, high-pass filters—eliminating strays and lower frequency signals and band-stop filters—eliminating strays and signals of frequency equal to strays frequency. Each kind of the above-mentioned filters interfers with and distorts the original waveform of the signals $U_{zs}$. Interference and distortions introduced by the said filters cause elimination not only of strays but also signals of component frequencies comprised in the evoked responses, as the responses usally comprise signals of frequencies comparable to the fundamental frequency of the strays.

The evoked response measuring sut-ups, known to us, described and manufactured by such companies as: NICOLET BIOMEDICAL CO.—USA, MEDELEC LIMITED—Great Britain, DISA ELEKTONIK A/S—Denmark, TECHNICAL UNIVERSITY OF WARSAW—Poland are only able to eliminate periodic strays by means of the averaging procedure, and in the case where the periodic strays $U_{zp}$ and the individual evoked responses $U_{ow}$ are synchronous, can be supported by the known filtering circuits.

SUMMARY OF THE INVENTION

An object of the invention is to provide a method and a circuit arrangement for substantially eliminating periodic strays in an averaging procedure while the original desired waveform is substantially undistorted.

According to one aspect of the invention, there is provided an averaging method for elimination of periodic strays in analog-digital computers employing an averaging procedure, in which method a set of signals $U_{zs}$ picked up by electrodes from an examined subject is processed to provide an averaged evoked response $\overline{U_{ow}}$ in order to reduce internal noise $U_{szw}$ and strays $U_{zp}$, originating in an environment comprising a main signal source, in proportion to the square root of the number N of sweeps of the averaging procedure, characterised in that periodic strays $U_{zp}$ are eliminated from the set of signals $U_{zs}$ during the averaging procedure in proportion to the number N of sweeps of the averaging procedure resulting in at least an N-fold reduction thereof by the introduction of desynchronization between a first waveform of frequency 1/T of external stimuli signals and a second waveform of frequency 1/t of the periodic strays by the introduction of an odd number K of half-periods of the second frequency 1/t, which number K determines the value of the period T according to the formula: $T=\frac{1}{2}tK$, where K is a natural and odd integer.

According to another aspect of the invention, there is provided a circuit arrangement in an evoked response measuring system for applying an averaging method for strays elimination comprising a triggering circuit connected to triggering inputs of an averaging computer and a stimulator and delivering common triggering pulses of frequency 1/T triggering successive sweeps of the averaging procedure in the averaging computer and simultaneously triggering successive external stimuli, such as photostimuli, from a stimulator, characterised in that the period T of the triggering pulses is determined from the sum of half-periods of periodic strays, from a main signal source, of frequency 1/T by a counting circuit by sensing the said periodic strays from an environment, comprising a main signal source, from which the waveform of the periodic strays is supplied to a sensing circuit comprising a transformer for stepping down the signal voltage and an analog filter, which at least partially prevents sporadic transient strays superimposed on the periodic strays from passing through the sensing circuit to further circuits, and said sensing circuit after stepping down the voltage and filtering the periodic strays supplies it to a half-period detecting circuit, which provides the counting circuit with pulses determining successive half-periods of the periodic signal, which is equivalent to the periodic strays induced in an examined subject from said environment.

Construction of a counting circuit for the evoked response measuring set-up is one aspect of the invention. The circuit employing the averaging method for elimination of the periodic strays prevents the measuring set-up from interfering with and distorting the original analog waveforms of the individual evoked responses $U_{ow}$ from the examined subject, and causes periodic strays $U_{zp}$ to be unambiguously eliminated from the averaged evoked responses $\overline{U_{ow}}$ in proportion to the number N of sweeps and thus the reduction is at least N-fold which means that the above-mentioned formula describing the averaged set of signals $\overline{U_{zs}}$ during the averaging procedure is as follows:

$$\overline{U_{zs}} = \frac{1}{N}\left[\sum_{n=1}^{N} U_{ow} + \frac{1}{N}\sum_{n=1}^{N} U_{zp} + \frac{1}{\sqrt{N}}\sum_{n=1}^{N} U_{szw}\right]$$

$$= \overline{U_{ow}} + \frac{1}{N}\overline{U_{zp}} + \frac{1}{\sqrt{N}}\overline{U_{szw}} \approx \overline{U_{ow}},$$

where $n=1, 2, 3, \ldots, N$; N at least several hundred.

As an example of the above situation, with 256 sweeps of the averaging procedure, the square root of N equals sixteen and the maximum amplitudes of the internal noise $U_{szw}$ and the periodic strays $U_{zp}$ are equal to 64 $\mu V$, then the sixteen-fold reduction in the averaging procedure is effective only in respect of the averaged internal noise $\overline{U_{szw}}$ resulting in it having maximum averaged amplitudes not greater than 4 $\mu V$, while the averaged periodic strays $\overline{U_{zp}}$ are reduced at least 256-fold leaving components with amplitudes not greater than 0.25 $\mu V$ in the set of the averaged signals and in an ideal case, when the periodic strays $U_{zp}$ and the individual evoked responses $U_{ow}$ are non-synchronous and number of N sweeps approaches infinity, the reduction value also approaches infinity and thus components of the averaged periodic strays $\overline{U_{zp}}$ approach zero.

The aim of the invention has been achieved by developing an averaging method based on elimination of the periodic strays $U_{zp}$ from the set of signals $U_{zs}$ during the averaging procedure to a greater extent, i.e. in proportion to the number N of sweeps of the averaging procedure, thus resulting in their at least N-fold reduction by introducing permanent desynchronization between the frequency 1/T of the external stimuli and the frequency 1/T of the periodic strays and by introducing an odd number K of half-periods of the said frequency 1/t, where K determines the value of the period T according to the formula: $T=\frac{1}{2}tK$, K being a natural and odd integer. The permanent desynchronization between the frequency 1/T of the external stimuli and the frequency 1/t of the periodic strays is realized by introducing a phase shift by angle $\alpha=180°$, which phase shift simultaneously corresponds to a time shift by one half-period of the said frequency 1/t of the periodic strays, which control periods of the external stimuli and initial phases of the periodic strays at the beginning of two successive periods of the external stimuli, or alternately at the beginning of two successive sweeps of the averaging procedure, differ by the value of the introduced phase shift while the period T of the triggering pulses is a result of summing of half-periods of the periodic strays, of frequency 1/T carried out by the counting circuit by sensing the said periodic strays from the environment, comprising a main signal source, from which by means of a cord supplying the measuring set-up, the sine wave signal of the strays periodic in this example, is fed to a sensing circuit comprising a transformer for stepping down the signal voltage and an analog filter, which at least partially prevents sporadic transient strays superimposed on the periodic strays from passing through the sensing circuit to further circuits. The sensing circuit, after stepping down the voltage and filtering the periodic strays, sends it along a direction connection to a half-period detecting circuit, which provides the counting circuit with pulses determining successive half-periods of the sine wave signal which is equivalent to the periodic strays induced in the examined subject from the environment comprising the main signal source of the periodic strays. The counting circuit is programmed by a circuit programming periods T with a given value of periods $T_z$. The value of the period T is approximately equal to the value of the period $T_z$ as the programming circuit finds an odd number K, which best approximates the result of $K \approx T_z \cdot 2/t$, which number K delivered to the counting circuit and stored there has the result that the circuit, after counting every K half-periods, provides the triggering circuit with pulses of frequency $1/t = 2/kt$.

The above-described way of achieving the aim of the invention has the following properties. Every consecutive external stimulus appearing after time T causes every sweep of the averaging procedure to be delayed by the time shift of one half-period of the periodic strays which means that the aforementioned strays $U_{zp}$ comprised in the set of signals $U_{zs}$ are also shifted in time by one half of its period t in respect to every individual evoked response $U_{ow}$, which response is also comprised in the said set of signals $U_{zs}$, the response considered is taken as that in the preceding period T in respect of the following one which is shown in FIGS. 3 and 4. The aforementioned time shift of one half of the period T secures permanent desynchronization between the periodic strays and the external stimuli, and consequently between the periodic strays and the individual evoked responses $U_{ow}$ and therefore the said strays are effectively eliminated in the averaging procedure proportionally to the number N of sweeps of the averaging procedure as illustrated in FIGS. 3 and 5.

The averaging method for periodic strays elimination and a counting circuit in an evoked response measuring set-up for applying the method is free from firm assumptions concerning the frequency 1/T of the external stimuli thanks to the counting circuit employed in the evoked response measuring system. The system has wide capabilities, especially in the few second range of the period T of the external stimuli because the method is not dependent on a tolerance of the frequency 1/t of the period strays, and in particular of the strays of the main signal source and more effectively reduces the said strays where an even number of N sweeps of the averaging procedure is applied.

Application of the averaging method for periodic strays elimination and of the counting circuit for the evoked response measuring system for applying the method is of particular importance for electrophysiological examinations to determine the degree of conduction loss of nervous paths between a sense organ and corresponding reception region of the cortex. Under unfavourable measuring conditions during a reception of e.g. visual evoked responses (individual evoked responses $U_{ow}$) the averaging procedure elicits from an electroencephalogram (internal noise $U_{szw}$) the aforementioned evoked responses recorded from the scalp (examined subject) activated by photo stimuli (external stimuli), there is the very often met a situation where the averaging procedure may also elicit remaining components of the strays from the main signal source eliciting them together with the individual evoked responses belonging to the set of signals $U_{zs}$ when the strays are in synchronism with sweeps of the averaging procedure. The counting circuit according to the invention prevents in every case the appearance of the said synchronism.

BRIEF DESCRIPTION OF THE DRAWINGS

For a better understanding of the invention, and to show how the same may be carried into effect, reference will now be made, by way of example, to the accompanying drawings, in which.

DESCRIPTION OF PREFERRED EMBODIMENT

Figure 3:
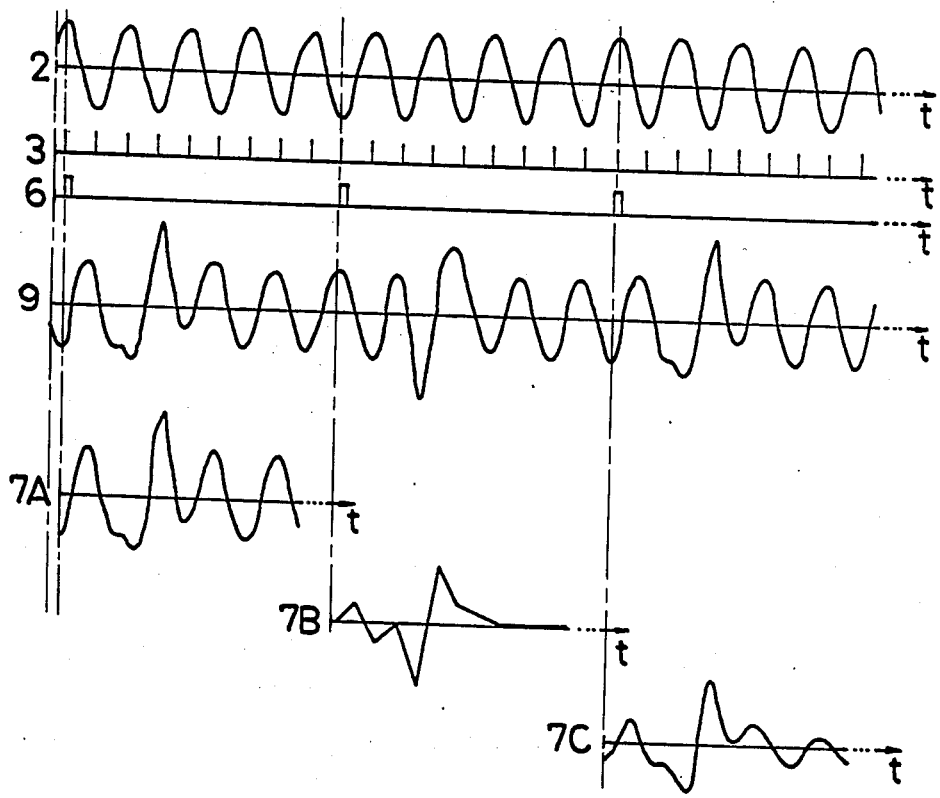
FIG. 3 shows electric signals related to the block diagram of FIG. 2.
Figure 4:
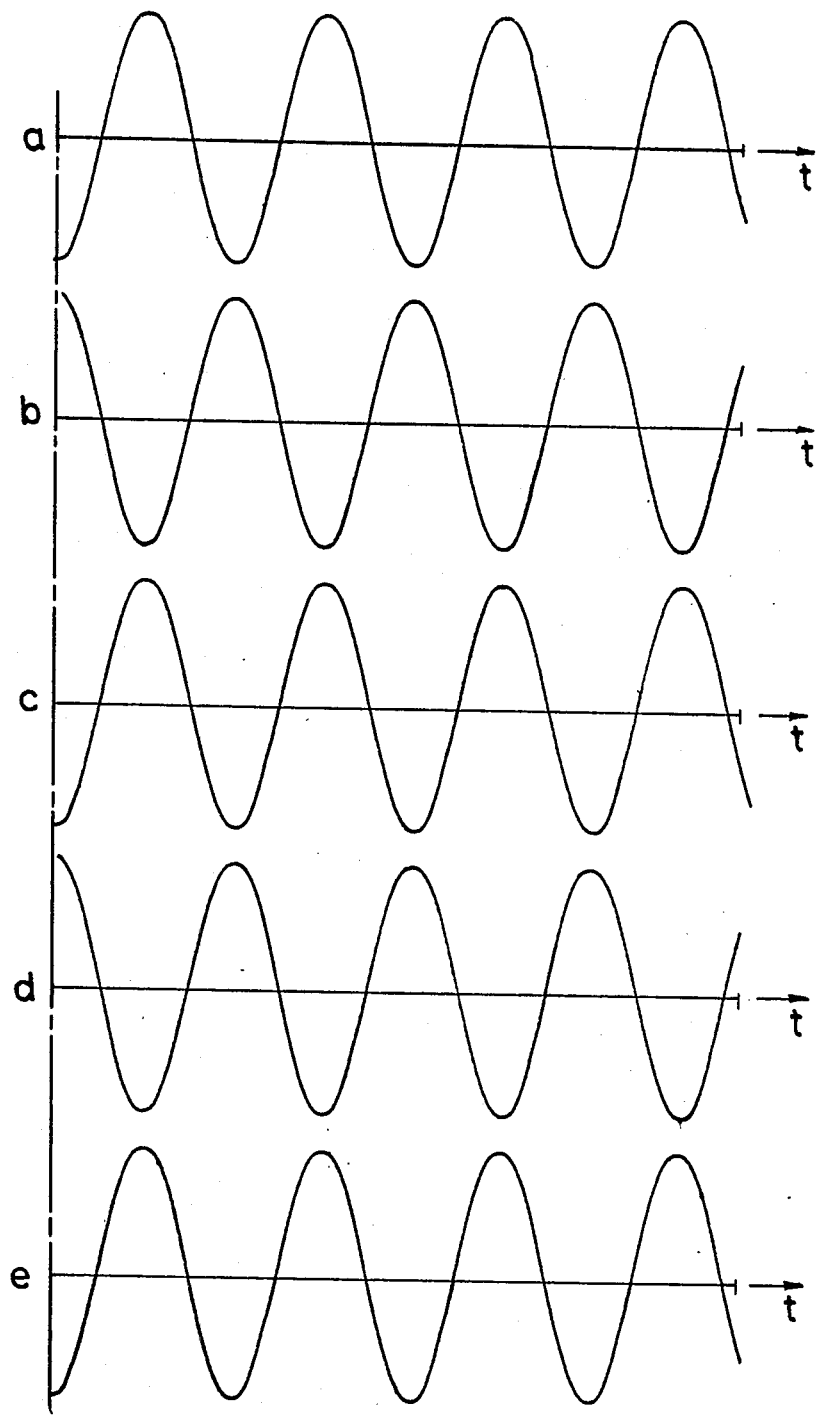
FIG. 4 illustrates successive signals of the periodic strays during the averaging procedure.
Figure 5:
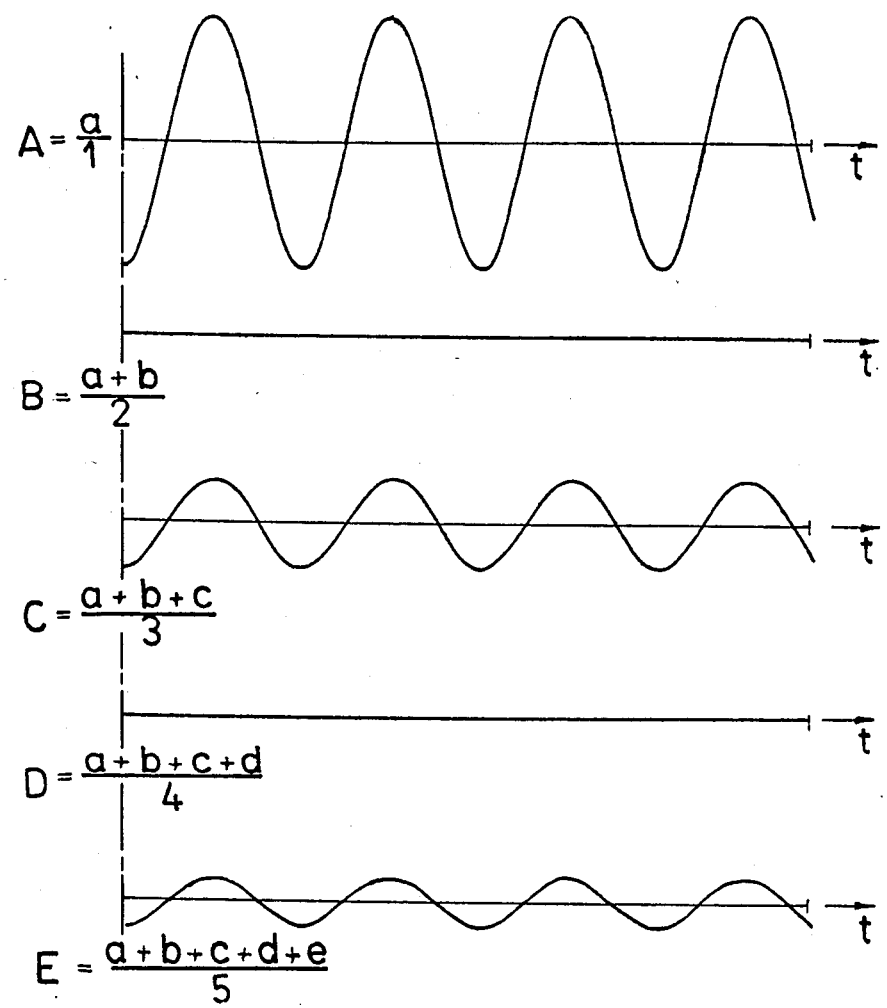
FIG. 5 illustrates successive sweeps of the averaging procedure as applied to the periodic stray signals shown in FIG. 4.

In FIGS. 4 and 5 the strays signal is shown alone to represent the desynchronized periodic strays in respect of successive pulses, which trigger successive sweeps of the averaging procedure and trigger the external stimuli which correspond to the sweeps and are correlated through the examined subject with the individual evoked responses, which responses and the internal noise are omitted for simplicity of the diagram. The internal noise has been also omitted in FIG. 3 to clarify the representation of successive sweeps of the averaging procedure by signals 7A, 7B and 7C.

The method of the periodic strays elimination according to the invention is based on the permanent desynchronization of the frequency 1/T of pulses which trigger successive sweeps of the averaging procedure after every external stimulus. A triggering pulse, shown as waveform 6 of FIG. 3, initiates both an external stimulus and a sweep of the averaging procedure. The desynchronization between the frequency 1/t of the strays and successive sweeps of the averaging procedure is based on the fact that the period T between consecutive external stimuli is determined each time by a number K of half-periods of the periodic strays of period t, i.e. $T = \frac{1}{2}tK$. The elimination of the said strays is conditioned by fulfilling the above formula for the sequence of numbers $K = 1, 3, 5, \ldots$, which means that if the periodic strays of frequency 1/t are superimposed on an individual evoked response and are shifted by angle $\alpha = 180°$ in relation to the preceding individual evoked response, total elimination of the periodic strays will occur. Accuracy of determining of the periodic strays half-periods has no practical significance, as discrepancy of the parameters can be so small, that the phase shift by angle $\alpha$ between successive sweeps may differ by single degrees, and the reduction of the said strays will be much more effective than is the case of the hitherto used averaging procedure, when the elimination is proportional to the number of N sweeps.

To exemplify the averaging method for periodic strays elimination in FIGS. 3, 4 and 5 the ideal phase shift of angle $\alpha = 180°$ is introduced and for better illustration of periodic strays elimintion in FIG. 5 two-fold magnificaiton of the amplitude scale in relation to the periodic stray signal being received during successive sweeps of the averaging procedure shown in FIG. 4 is introduced. In addition, the desynchronized sinusoidal strays picked up together with the internal noise $U_{szw}$ and the individual evoked responses $U_{ow}$ during each sweep of the averaging procedure are shown in waveform 2 of FIG. 3 and waveforms a through e of FIG. 4, and they all are repeated in successive time intervals between every two successive external stimuli of frequency 1/T, which time intervals correspond to sweeps of the averaging procedure. The said sweeps of the averaging procedure are shown in FIG. 5, where waveform "A" represents the first sweep corresponding to periodic stray waveform a of FIG. 4, waveform "B" represents the second sweep of the averaging procedure corresponding to the cumulation of waveforms a and b of FIG. 4, and during the second sweep the first total elimination of the periodic strays takes place and further waveforms "C", "D" and "E" are results of the successive sweeps of the averaging procedure, and during the fourth sweep the second total elimination of the periodic strays takes place. In an example case of the phase shift by $\alpha = 180°$ total elimination of the periodic strays takes after every second successive sweep of the averaging procedure, which sweeps are counted starting from the waveform "A" as the first sweep.

Description of the averaging method for periodic strays elimination, in a practical case, requires a detailed discussion which uses some example data, since the periodic strays may be in particular from a main signal source with various values of the nominal frequency $1/t_n$ depending on the place and examination conditions and may be e.g. 50 c/s, 60 c/s, 400 c/s, etc.

For example signal generating environment may be a source of the periodic strays in form of the sinusoidal signal of the nominal frequency $1/t_n = 50$ c/s with the admissible tolerance $$\pm \Delta \frac{1}{t_n} = 1 \text{ c/s}$$

which means that the period t of the strays at a given moment of the examination procedure may be of any value comprised within the tolerance interval $t_{min} = 19.6$ ms $\leq t \leq 20.4$ ms $= t_{max}$. To determine an odd number of K one must assume an experimental frequency $1/T_z$ or an experimental period $T_z$, e.g. $T_z = 3$ s and then correct the value in respect to an odd multiple of the number of K of the half-periods of the nominal frequency $1/t_n$ of the periodic strays:

$$K_z = \frac{2T_z}{t_n} = \frac{2 \cdot 3 \, s}{20 \, ms} = 300,$$

since the resulting $K_z$ is an even number and according to the assumption the number must be odd, one makes the $K_z$ odd in an arbitrary way so that the $K_z$ may be here 301, which causes, that in this case taking into account the tolerance of the periodic strays frequency the T may be comprised within the interval $2.9498$ s $\leq T \leq 3.0702$ s according to the following formula $T_{min} = \frac{1}{2} t_{min} K = \frac{1}{2} 19.6$ ms$\cdot 301 = 2.9498$ s and $T_{max} = \frac{1}{2} t_{max} K = \frac{1}{2} 20.4$ ms$\cdot 301 = 3.0702$ s. The above interval within which the period T may be comprised is so narrow that it has no practical meaning for the assumed value of the period $T_z$.

The aforementioned averaging method for periodic strays elimination enables design of the above-described evoked response measuring system, which comprises a circuit for counting half-periods of the strays which circuit determines the period T of the external stimuli, which are in each case non-synchronous with the periodic strays from the main signal source.

Figure 1:
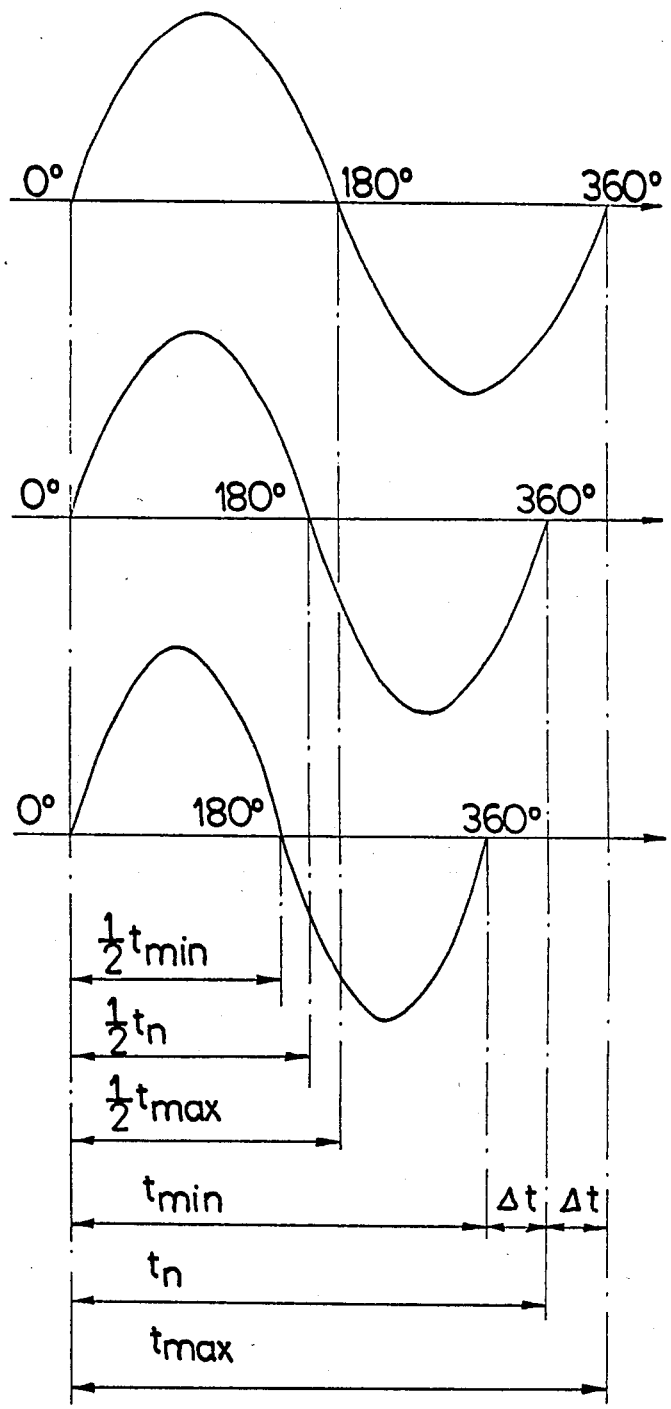
FIG. 1 illustrates relations between angle and time parameters of sinusoidal periodic strays.
Figure 2:
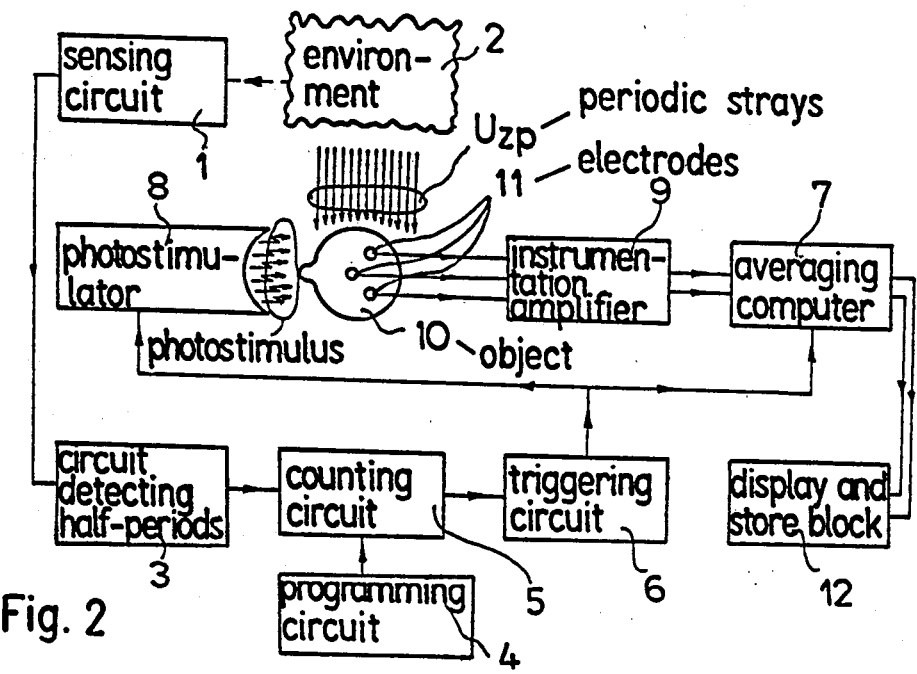
FIG. 2 shows a block diagram of the evoked response measuring set-up employing the averaging method.

The system for measuring evoked responses, in particular for measuring visual evoked responses for applying the above-described method, is illustrated in FIG. 2 with the corresponding waveforms of the circuit displayed in FIG. 3, and is provided with a circuit 1 sensing the periodic strays $U_{zp}$ coming from an environment 2 comprising a source of the periodic strays of frequency 1/t, which strays sensed by the circuit 1 come directly from the main signal source; a circuit 3 detecting half-periods of the periodic strays, a circuit 4 programming the period T of the external stimuli, which circuit sets a circuit 5 to count a proper number of K half-periods, a circuit 6 triggering simultaneously successive sweeps of the averaging procedure in an averaging computer 7 and pertinent successive external stimuli, an electroluminescent matrix of a photostimulator 8, the photostimulator 8 being equipped with the electroluminescent matrix, as a source of the external stimuli, an instrumentation amplifier 9 for amplifying the set of signals $U_{zs}$, which signals are picked up from an examined subject 10 e.g. a human scalp by means of electrodes 11 of Ag-AgCl type, the averaging computer 7 running the averaging procedure of the set of signals, and a memory and display block 12 for storing and displaying results of the averaging procedure.

Operation of the evoked response measuring system for applying the averaging method for periodic strays elimination is described below in reference to FIG. 2.

The strays, shown in waveform 2 of FIG. 3, coming from the environment 2 comprising a source of the strays, in this example a main signal source, are sensed directly in the source by means of a line supplying the whole system and the signal picked up in this way is fed directly to the sensing circuit 1. The circuit 1 sensing the periodic strays comprises a stepdown transformer, from which the periodic strays in form of a sinusoidal signal with voltage of several volts are fed to a low-pass filter to prevent the appearance of sporadic transient strays superimposed on the periodic strays, and are then fed through a sensing circuit to further circuits. Then the thus filtered strays are sent to the circuit 3 which detects half-periods of the sinusoidal periodic strays, and produces pulses, shown as waveform 3 of FIG. 3, corresponding to every positive and negative peak of the waveform of the periodic strays. Counting circuit 5 is provided with the pulses and counts them until the number programmed by the circuit 4—programming the period of the external stimuli—is reached. The programming circuit determines a pertinent number K corresponding approximately to the ratio of the period T of the external stimuli to the half-period $\frac{1}{2}t$ of the periodic strays, and the chosen K is always an odd number. The aforementioned counting circuit 5 produces a pulse after every K half-periods, which pulse is sent directly to the circuit 6, which triggers directly the photostimulator 8 and the averaging computer 7. The photostimulator 8, triggered by each pulse, shown in waveform 6 of FIG. 3, from the circuit 6 generates the external stimuli in form of the photostimuli which through the eye and visual nervous path of the subject produce an electrophysiological response in pertinent regions of the cortex. The electrophysiological response corresponds to an individual evoked response $U_{ow}$ which is picked up by the electrodes 11 placed on the scalp of the examined subject 10. The individual evoked response $U_{ow}$ is picked up together with the internal noise $U_{szw}$, in this case being called an electroencephalogram, and with the periodic strays $U_{zp}$ originating from the environment 2. The set of signals, one channel of which is shown as waveform 9 of FIG. 3, is fed to differential inputs of the circuit 9 the two channel instrumentation amplifier. The circuit 9 in each of its channels amplifies the set of signals $U_{zs}$ to match its output voltage with a voltage range of analog inputs of the averaging computer 7. Each triggering pulse starts successive sweeps, three of those sweeps being shown as waveforms 7A, 7B and 7C and FIG. 3, of the averaging procedure for the set of signals $U_{zs}$.

The averaged set of signals $\overline{U_{zs}}$ equals the averaged evoked response $\overline{U_{ow}}$. The product of averaging of the set of signals $U_{zs}$ in the averaging computer 7 is sent from the computer to the block 12—memory and display to provide a possibility for future display and selection of a result and to provide data for further statistical analysis with the use of a larger digital computer.

An application of the averaging method for periodic strays elimination and of the counting circuit in the system for measuring evoked responses for employing the method is of particular significance in case of electrophysiological examinations, which determine the degree of deterioration in nerve conduction pathways linking a sense organ and a pertinent reception area of cortex, and especially during reception of visual evoked responses.

We claim:

1. An averaging method for elimination of periodic strays in averaging devices and computers employing an averaging procedure in electrophysiological analysis of a subject, the method comprising the steps of:

stimulating the subject through the use of stimulation means;

sensing a set of signals from the subject by means of electrodes, the set of signals consisting of internal noise and individual evoked responses of an examined subject as well as periodic strays induced in the subject from an environment;

amplifying the set of signals with an instrumentation amplifier;

transmitting the set of signals to an averager;

eliminating the internal noise through the use of an averaging procedure in an averager;

said averaging procedure using a number N of stimuli repetitions to reduce the internal noise through reinforcement of the periodic evoked response signal while achieving at least a square root of N signal-to-noise ratio reduction through non-reinforcement of the random internal noise;

sensing a periodic stray signal with frequency 1/t from the environment with a sensing circuit;

supplying the periodic stray signal to a half-period detecting circuit;

determining the half-period of the periodic stray signal in the detecting circuit;

generating half-period pulses of frequency 2/t in the detecting circuit;

transmitting the half-period pulses to a counting circuit;

counting the half-period pulses in the counting circuit;

determining a triggering frequency 1/T in a programming circuit, T being equal to the half-period multiplied by an odd natural number which is chosen to allow a period as close as possible to a selected length;

transmitting the pulses of frequency 1/T to a triggering circuit;

initiating the averaging procedure with frequency 1/T in a triggering circuit;

sending simultaneous initiation signals from the triggering circuit to the averager and to the stimulation means;

the method resulting in the reduction of periodic stray signals in proportion to the number of stimulus repetitions, N.

2. An averaging method according to claim 1, wherein the phase of the periodic strays of frequency 1/t, at the beginning of two consecutive sweeps of the averaging procedure in an averager, is shifted by an angle equal to 180°.

3. A circuit for elimination of periodic strays, comprising a triggering circuit, connected in parallel to the input of an averager and a photostimulator, wherein a triggering circuit is connected in series to a counting circuit, being independently connected to a programming circuit and half-periods detecting circuit, being in turn connected in series to periodic strays sensing circuit.

* * * * *